(12) United States Patent
Li et al.

(10) Patent No.: US 8,338,616 B2
(45) Date of Patent: Dec. 25, 2012

(54) THIAZOLIUMS AND THEIR USE FOR TREATING PROTEIN AGING ASSOCIATED DISEASES

(75) Inventors: Song Li, Beijing (CN); Wu Zhong, Beijing (CN); Lili Wang, Beijing (CN); Zhibing Zheng, Beijing (CN); Hao Cui, Beijing (CN); Junhai Xiao, Beijing (CN); Gang Cheng, Beijing (CN); Yunde Xie, Beijing (CN); Bing Zhang, Beijing (CN)

(73) Assignee: Beijing Molecule Science And Technology Co., Ltd., Beijing (CN)

( * ) Notice: Subject to any disclaimer, the term of this patent is extended or adjusted under 35 U.S.C. 154(b) by 0 days.

(21) Appl. No.: 13/120,009

(22) PCT Filed: Sep. 15, 2009

(86) PCT No.: PCT/CN2009/001036
§ 371 (c)(1), (2), (4) Date: Mar. 25, 2011

(87) PCT Pub. No.: WO2010/031248
PCT Pub. Date: Mar. 25, 2010

(65) Prior Publication Data
US 2011/0178141 A1    Jul. 21, 2011

(30) Foreign Application Priority Data
Sep. 22, 2008  (CN) .......................... 2008 1 0211657

(51) Int. Cl.
*A61K 31/426*  (2006.01)
*C07D 277/30*  (2006.01)

(52) U.S. Cl. ...................... 548/204; 514/365
(58) Field of Classification Search ............... 548/204
See application file for complete search history.

(56) References Cited

U.S. PATENT DOCUMENTS

| | | | |
|---|---|---|---|
| 5,449,680 A * | 9/1995 | Solomon et al. | 514/365 |
| 2005/0245512 A1 | 11/2005 | Ulrich et al. | |
| 2009/0227643 A1 | 9/2009 | Li et al. | |

FOREIGN PATENT DOCUMENTS

| | | | |
|---|---|---|---|
| CA | 2640396 A1 * | 8/2007 | |
| CA | 2210684 C | 1/2008 | |
| CN | 1534027 A | 10/2004 | |
| WO | WO-03/072557 A1 * | 9/2003 | |
| WO | WO-2005/021519 A2 * | 3/2005 | |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Gould, International Journal of Pharmaceutics, 33 (1986), pp. 201-217.*
PCT/CN2009/001036 International Search Report dated Dec. 24, 2009.
Translation of Abstract for CN 1185736 (A), 1998.
Larsen, Scott D. et al., Synthesis and Biological Activity of Analogues of the Antidiabetic/Antiobesity Agent 3-Guanidinoropionic Acid, Journal of Medicinal Chemistry, vol. 44, No. 8, pp. 1217-1230 (2001).
Supplementary European Search Report for Application No. EP 09 81 3969 (Jan. 19, 2012).

* cited by examiner

*Primary Examiner* — Laura L. Stockton
(74) *Attorney, Agent, or Firm* — MacMillan, Sobanski & Todd, LLC

(57) ABSTRACT

The present invention relates to a composition of a thiazolium compound of formula I or a solvate thereof, wherein the definitions of groups in the formula I are as those given in the claims:

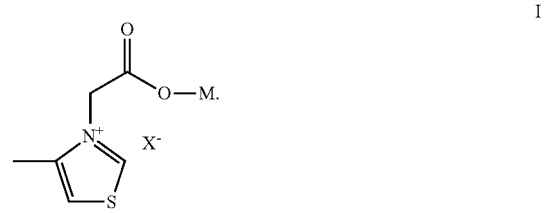

5 Claims, 1 Drawing Sheet

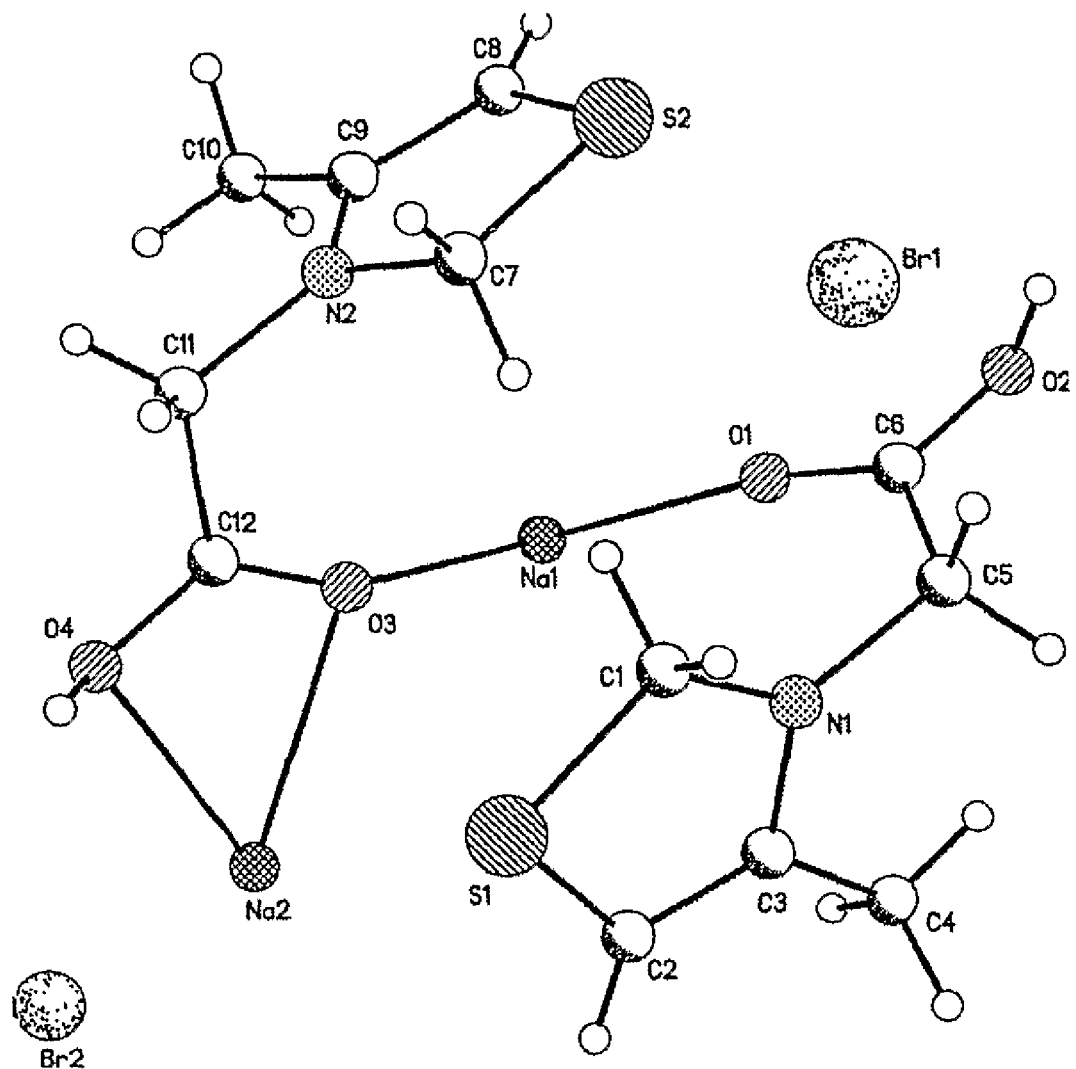

THIAZOLIUMS AND THEIR USE FOR TREATING PROTEIN AGING ASSOCIATED DISEASES

CROSS-REFERENCE TO RELATED APPLICATIONS

This application is the National Phase of International Application PCT/CN2009/001036 filed Sep. 15, 2009, which designated the U.S. That International Application was published in English under PCT Article 21(2) on Mar. 25, 2010 as International Publication Number WO 2010/031248A1. PCT/CN2009/001036 claims priority to Chinese Application No. 200810211657.7 filed Sep. 22, 2008. Thus, the subject nonprovisional application also claims priority to Australian Application No. 200810211657.7 filed Sep. 22, 2008. The disclosures of both applications are incorporated herein by reference.

TECHNICAL FIELD

The present invention relates to a thiazolium compound, a process for preparing the compound, a composition comprising the compound as an active component and a pharmaceutically and/or cosmetically acceptable carrier, excipient or diluent, and use of the compound for preventing or treating diseases or symptoms associated with AGEs (Advanced Glycosylation Endproducts, AGEs); for (i) improving skin elasticity or reducing skin wrinkles, (ii) for treating diabetes, (iii) for treating or relieving a sequela of diabetes, (iv) for treating or relieving a kidney injury, (v) for treating or relieving a vascular injury, (vi) for treating or relieving hypertension, (vii) for treating or relieving retinopathy, (viii) for treating or relieving a lens protein injury, (ix) for treating or is relieving cataract, (x) for treating or relieving peripheral nerve diseases, (xi) for treating or relieving osteoarthritis; for improving sclerosis of the cardiovascular system; for increasing sensitivity to a cardiovascular medication in senior and diabetic patients; for treating chronic heart failure; for manufacturing an oral preparation for preventing or reversing tooth staining; or for manufacturing an anti-staling agent for plant proteins of various crops and animal proteins.

BACKGROUND ART

Chinese Patent for invention CN200610002391.6 discloses a class of thiazoliums, such as 3-benzyloxycarbonylmethyl-4-methyl-thiazole-3-bromide represented by Formula III,

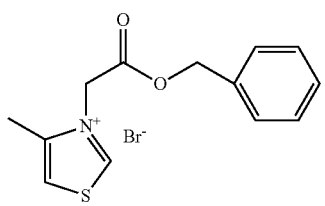

(Formula III)

Comprehensive pharmacokinetic studies of 3-benzyloxycarbonylmethyl-4-methyl-thiazole-3-bromide in rats by oral administration and in beagles by oral administration, and the tissue distribution in vivo of the compound in mice show that the compound has an excellent breaking effect on AGEs. However, it is still desirable to develop and search compounds more simple in structure having an excellent breaking effect on AGEs.

Contents of the Invention

The object of the invention is to search and develop a small molecular breaker of AGEs for breaking the already formed AGEs so as to prevent protein cross-linking, breaking the cross-linked proteins so as to promote protein metabolism, and further improving various pathological changes resulted from the elevated level of AGEs in vivo, including increasing skin elasticity or is reducing skin wrinkles, treating diabetes, or treating or relieving a sequela of diabetes, kidney injury, vascular injury, hypertension, retinopathy, lens protein injury, cataract, peripheral nerve diseases or osteoarthritis; or improving sclerosis of the cardiovascular system; or treating chronic heart failure; or increasing sensitivity to a cardiovascular medication in senior and diabetic patients. Also, the glycosylated proteins on which the breaker of cross-linked structure in proteins acts are not limited to human proteins, but also include plant proteins of crops or animal proteins, thus the breaker can be further useful for the fresh-keeping of plant proteins of crops and animal proteins.

It has been found by the present inventors that the compound of Formula I can be useful for the treatment and/or prevention of many diseases caused by glycosylation of proteins; for the improvement of sclerosis of the cardiovascular system; for the increasing sensitivity to a cardiovascular medication in senior and diabetic patients; or for the treatment of chronic heart failure.

It has also been found that a composition of the compound of Formula I or a solvate thereof has a comparable breaking activity on AGEs and more stable pharmacokinetic properties in comparison with the preferred compound 3-benzyloxycarbonylmethyl-4-methyl-thiazole-3-bromide (see Formula III) as disclosed in CN200610002391.6.

Hence, the first aspect of the present invention relates to a compound of Formula I or a solvate thereof,

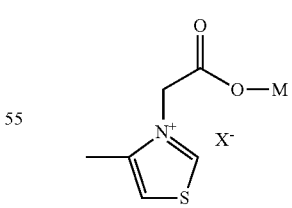

I wherein:
M is Na or K; and
X is Br, Cl or I.

Another aspect of the present invention relates to a process for preparing a compound of Formula I, comprising:

a) reacting 4-methylthiazole with chloroacetic acid or bromoacetic acid

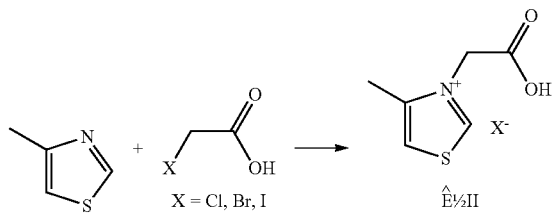

wherein X is Br or Cl or I;

b) reacting the compound of Formula II with a base to obtain a compound of Formula I

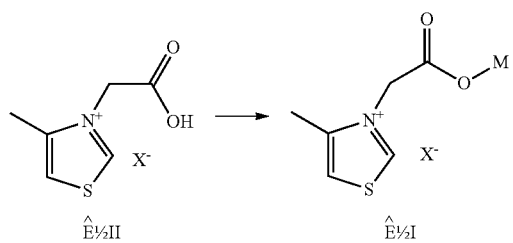

wherein:

M is Na or K; and

X is Br or Cl or I.

The base used in the above method includes but is not limited to sodium hydroxide, sodium hydrogen carbonate, sodium carbonate, potassium hydroxide, potassium carbonate.

Further another aspect of the present invention relates to a composition, comprising at least one compound of Formula I or a solvate thereof, a carrier or excipient commonly used in composition. The carrier or excipient includes but is not limited to carriers or excipients commonly used in pharmaceutics, cosmetics or foods.

One aspect of the present invention relates to a use of at least one compound of Formula I or a solvate thereof for manufacturing a medicament for the prophylaxis and/or treatment of various diseases caused by protein glycosylation.

The present invention further relates to a method for prophylaxis and/or treatment of various diseases caused by protein glycosylation, comprising administering a patent in need of the prophylaxis and/or treatment with an prophylactically and/or therapeutically effective amount of at least one compound of Formula I or a solvate thereof.

The glycosylated proteins, on which the breaker of the present invention acts, are not limited to human proteins, but also include plant proteins of crops or animal proteins, thus the breaker of the present invention or a composition thereof can be further used for fresh-keeping.

According to the present invention, the compound of Formula I of the present invention or a solvate thereof is preferable the following compounds:

| Compound | Chemical name | Structure | m.p. °C. |
|---|---|---|---|
| 1 | 3-carboxymethyl-4-methyl-thiazolium bromide sodium salt | 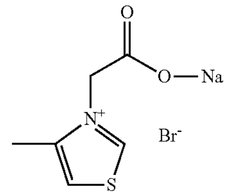 | 182 |
| 2 | 3-carboxymethyl-4-methyl-thiazolium chloride sodium salt | 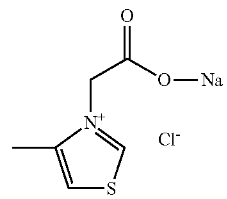 | 210 |

The composition of the present invention can be, for example, pharmaceutical composition or cosmetic composition or in other forms.

The pharmaceutical composition of the present invention comprises an effective amount of a compound of Formula I of the present invention or a solvate thereof and one or more suitable pharmaceutically acceptable carriers. Said pharmaceutically acceptable carriers include but are not limited to: ion exchangers, alumina, aluminum stearate, lecithin, serum proteins such as human serum albumin, buffers such as phosphates, glycerin, sorbic acid, potassium sorbate, mixtures of saturated vegetable fatty acids partially is esterified with glycerin, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulosic materials, polyethylene glycol, sodium carboxymethylcellulose, polyacrylate, beeswax, and lanolin.

The compounds of the present invention are a class of potent breaker for cross-linked proteins, have good ability of breaking glycosylated proteins, and thus can be used in, but not limited to, (i) increasing skin elasticity or reducing skin wrinkles, (ii) for treating diabetes, (iii) for treating or relieving sequela of s diabetes, (iv) for treating or relieving a kidney injury, (v) for treating or relieving a vascular injury, (vi) for treating or relieving hypertension, (vii) for treating or relieving retinopathy, (viii) for treating or relieving a lens protein injury, (ix) for treating or relieving cataract, (x) for treating or relieving peripheral nerve diseases, (xi) for treating or relieving osteoarthritis.

The compounds of the present invention can well improve sclerosis of the cardiovascular system.

The compounds of the present invention can well improve the sensitivity to cardiovascular medication in senior and diabetic patients.

The compounds of the present invention can be used for treating chronic is heart failure.

The compounds of the present invention can be further used for preventing or reversing tooth staining caused by non-enzymatic glycosylation in oral cavity. The dosage schedule of the compounds of the present invention can be altered according to the intended uses.

The non-enzymatic reaction which occurs in the oral cavity can result in tooth staining. Presently used anti-plaque agents can accelerate this glycosylation reaction and further the staining of the teeth. Recently, a class of cationic bactericides with anti-plaque properties have been used in conventional oral cleaning. These cationic bactericides include alexidine, cetyl pyridinium chloride, and so on. These agents can accelerate a key step in the glycosylation reaction, i.e. Maillard reaction, to thereby accelerate tooth staining (Nordbo, J. Dent. Res., 58:1429 (1979)). Moreover, it is reported that it is observed in vitro that chlorhexidine and benzalkonium chloride can catalyze glycosylation reaction (browning reaction). Chlorhexidine added to mixtures containing a sugar and an amino acid accelerates color formation, attributed to the Maillard reaction.

Due to the above reasons, the compounds of the present invention and pharmaceutical compositions comprising the same can be used in oral cavity. Particularly suitable formulations are oral rinses and toothpastes incorporating the agents.

As for the above mentioned use of the compounds of the present invention, non-toxic and pharmaceutically acceptable carriers in appropriate forms can be used to formulate such oral rinses and toothpastes.

The pharmaceutical compositions comprising the compounds of the present invention can be administered in any of the following manners: oral administration, spraying-inhaling, rectal administration, nasal drug delivery, buccal administration, topical administration, parenteral administrations such as subcutaneous, intravenous, intramuscular, intraperitoneal, intrathecal, is intraventricular, intrasternal and intracranial injection or infusion, or explantation reservoir administration, wherein oral administration, intraperitoneal or intravenous administrations are preferred.

For oral administration, the compounds of the present invention can be formed into any dosage forms suitable for oral administration, including but not limited to tablets, capsules, solutions in water or suspensions in water. The carriers useful in the tablet formulations generally include lactose and corn starch, and lubricants such as magnesium stearate can also be used. Diluents useful in the capsule formulations generally include lactose and dry corn starch. Aqueous suspension formulations are generally formed by mixing active components with proper emulsifiers and suspension agents. When needed, sweeteners, flavoring agents or colorants can be added to said oral formulations.

For topical administration, especially for the treatment of suffering surfaces or organs where external applied medicaments can easily reach, such as eye, skin or lower intestine, the compounds of the present invention can be formed into various formulations suitable for topical administration depending on the suffering surfaces or organs. Detailed explanation is as follows:

When topically administered to the eye, the compounds of the present invention can be formulated into the form of micronization suspensions or solutions, wherein the carrier used is an isotonic sterile saline of a certain pH, with/without a preservative such as benzyl alkanol chloride. When administered to the eye, the compounds can also be formulated into ointment such as vaseline ointment.

When topically administered to the skin, the compounds of the present invention can be formulated into suitable forms such as ointment, lotion, or cream, wherein active components are suspended or dissolved in one or more carriers. The carriers used in the ointment formulations include, but are not limited to, mineral oil, liquid petrolatum, petrolatum album, propylene glycol, is polyethylene oxide, polypropylene oxide, emulsifying wax, and water. The carriers used in the lotion or cream formulations include, but are not limited to, mineral oil, sorbitan monostearate, Tween 60, cetyl ester wax, oleyl aromatic alcohol, 2-octyl dodecanol, benzyl alcohol, and water.

The compounds of the present invention can also be administered in the form of sterile injectable preparations, including sterile injectable water or oil suspension, and sterile injectable solution. The carriers and solvents that can be used include water, Ringer's solution and isotonic sodium chloride solution. Sterile non-volatile oils such as monoglycerides or diglycerides can also be used as solvents or suspension media.

Additionally, it should be pointed out that the dosage and administration method of the compounds of the present invention are dependent on many factors, including age, body weight, gender, physical health state, nutritional status of the subject, the activity of the compounds to be used, the period of time of application, metabolic rate, severity of the disease, and the subjective judgment of the doctor. The preferred dosage is in a range of from 0.01 to 100 mg/kg body weight/day, and the most preferred dosage is in a range of from 20 to 30 mg/kg body weight/day.

BRIEF DESCRIPTION OF THE DRAWINGS

FIG. 1 is a X-ray diffraction structural diagram of 3-carboxymethyl-4-methyl-thiazolium bromide sodium salt.

EXAMPLES

The following examples are given to illustrate the preferable embodiments of the present invention and by no means intended to limit the scope of the present invention.

Melting points of the compounds were measured by SRY-1 model melting point instrument, and the temperature was not corrected. $^1$H-NMR spectra were measured by Bruker ARX400 or US Varian Unity Inova 600 model NMR is spectrometer, and FAB mass spectra were measured by Zabspect high resolution mass spectrometer.

Example 1

Preparation of 3-carboxymethyl-4-methyl-thiazolium bromide 15.6 g of 4-methylthiazole was dissolved in 50 ml of anhydrous acetone. The mixture was added with 21 g of bromoacetic acid, stirred for 3 d, filtered to obtain a solid, and a white solid was then obtained by recrystallization from ethanol, and dried to obtain 26 g product with a yield of 72%, mP=240.6-241.6° C.

MS[M]$^+$=158.2 m/e; $^1$H-NMR (400 MHz,DMSO) 2.48(d, 3H); 5.55(s,2H); 8.09(d,1 H); 10.25 (d,1 H), 14.05 (brs,1 H).

Example 2

Preparation of 3-carboxymethyl-4-methyl-thiazolium chloride 15.6 g of 4-methylthiazole was dissolved in 50 ml of anhydrous acetone. The mixture was added with 15 g of chloroacetic acid, stirred for 5 d, filtered to obtain a solid, and a white solid was then obtained by recrystallization from ethanol, dired to obtain 20.4 g product with a yield of 66.9%, mP=262.3-263.6° C.

MS[M]+=158.2 m/e; $^1$H-NMR (400 MHz,DMSO) 2.42(d, 3H); 4.84(s,2H); 7.93(d,1 H); 10.01 (d,1 H), 13.98 (brs,1 H).

Example 3

Preparation of 3-carboxymethyl-4-methyl-thiazolium bromide sodium (A)

20 g of 3-carboxymethyl-4-methyl-thiazolium bromide as a white solid was suspended in 90-100 ml of anhydrous methanol. The suspension was then added with an equimolar amount of sodium hydrogen carbonate, stirred at room temperature for 8 h, filtered, and the mother liquor was added with 150 ml of anhydrous ethanol, and stood to precipitate a crystal, to obtain 15 g product as a white crystal having a yield of 75%.

MS[M]+=158.2 m/e; 1H-NMR (400 MHz,DMSO) 2.50(d, 3H); 4.82(s,2H); 7.93(d,1 H); 10.00 (d,1 H).

Element analysis: $C_6H_7NO_2SBr$(260.08), theoretical values: C, 27.71; H, 2.71; N, 5.39; Br, 30.72%

Observed values: C, 27.50; H, 2.836; N, 5.304; Br, 30.891

Measurement of Crystal Structure by X-Monocrystal Diffraction 5 mg of 3-carboxymethyl-4-methyl-thiazolium bromide sodium as a white crystal was dissolved in 1 ml of anhydrous ethanol with heating to obtain a colorless solution. The solution was filtered, the filtrate stood in an calorstat oven at 30° C. for 5 d, and a white columnar crystal was slowly precipitated. After the crystal grain grew slowly to form a monocrystal, its crystal structure was measured by using the X-ray monocrystal diffractometry. The structure is shown in FIG. 1.

Crystallographic data: $C_{12}H_{14}Br_2N_2Na_2O_4S_2$, Mr=520.20, triclinic stystm space group P-1, crystallographic parameters: a=8.9000(18)A, α=92.82(3) deg., b=9.4095(19)A, β=109.00(3) deg., c=12.028(2)A, δ=104.11(3) deg.

Example 4

Preparation of 3-carboxymethyl-4-methyl-thiazolium chloride sodium 20 g of 3-carboxymethyl-4-methyl-thiazolium chloride as a white crystal was suspended in 90-120 ml of anhydrous methanol. The suspension was then added with an equimolar amount of sodium hydrogen carbonate, stirred at room temperature for 8 h, filtered, the filtrate was then added with 150 ml of anhydrous ethanol, and stood to precipitate a crystal to obtain 19 g of product as a white crystal having a yield of 79%.

Example 5

ELISA Screening Test for Breaking AGE-BSA-Collagen Crosslinked Structures

AGE cross-link structures were prepared in vitro by cross-linking AGE-BSA to rat tail collagen coated on a 96 well ELISA plate. A ELISA method was used to evaluate the breaking effect of the compounds on AGE cross-links.

Preparation of the tail collagen coated 96 Well ELISA Plates:

Normal Wister rats (body weight of 200±20 g) were sacrificed acutely, the tails were excised, and tail collagen was prepared at a temperature of 4° C. as follows. Tail tendon collagen fibrils were taken out, washed with physiological saline, peeled off non-collagen fibril tissues, rinsed with double-distilled water 3 times, cut into pieces, and immersed in 0.1% glacial acetic acid at 4° C. for one week during which it was shaken frequently. Finally, the immersion liquid was subjected to a centrifuge at 8000 g for 30 minutes, and the supernatant collagen solution was collected. After dilution, the protein content was measured. 96 well ELISA plates (Costar) were full-well coated with a collagen solution in an amount of 70 μg collagen per well at 4° C. for 24 hours, then the coating solution was discarded. The plates were air dried under sterile condition, coated with an anti-staling film, and finally stored at 4° C. for use.

Preparation of AGE-BSA:

A solution containing 50 mg/ml of bovine serum albumin BSA (V) (Roch) and 0.5M of glucose in 0.2M PBS (pH 7.4) was incubated in dark at 37° C. under sterile condition for 3-4 months, to thereby form glycosylated BSA, i.e. BSA-AGE. At the same time, non-glycosylated BSA was prepared with glucose-free BSA. Then the BSA-AGE solution was dialyzed against 0.01 M PBS (pH 7.4) to be removed of unreacted glucose. Fluorescence scanning (Exi/Em (395/460 nm)) and SDS-PAGE were used to check the formation of BSA-AGE, and protein concentration was determined by the Lowery method.

Assay Protocol:

The tail collagen coated 96 well ELISA plates were full-well treated with PBS (pH 7.4) for 1 hour to neutralize the acidic collagen. Then the plates were blocked with Superblock (PIERCE) at 37° C. for 1 hour, and washed with PBST (PBS-Tween) three times while shaking for 1 minute for each time of washing. AGE-BSA was diluted in PBS to a concentration required to obtain maximum cross-linking. 100 μl of the AGE-BSA solution was added to wells in the rows labeled as A, B, C, and D of the 96 well plates, and BSA solution of the same concentration was added to wells in the rows labeled as E, F, G, and H. The first three wells in each row were filled with PBS for the reagent blank. The plates were incubated at 37° C. for 4 hours to allow the collagen crosslink, and washed with PBST four times while shaking for 1 minute for each time of washing. Test compounds were diluted in PBS of pH 7.4. A test compound was added to quadruplicate AGE-BSA cross-links wells and quadruplicate BSA wells in an amount of 100 μl/well. PBS was added in an amount of 100 μl/well in the same way as non-breaking contrast. The plates were incubated at 37° C. for 16 hours and washed four times with PBST while shaking for 1 minute for each time of washing. 80 μl/well of Rabbit-anti-BSA antibody (1:500) was added to the wells and the plates were incubated at 37° C. for 50 minutes. After the plates were washed with PBST four times while shaking for 1 minute for each time of washing, 80 μl/well of horse radish peroxidase labeled goat anti-rabbit IgG (1:1000) was added to the wells. The plates were incubated at 37° C. for 50 minutes, and then washed with PBST three times while shaking for 1 minute for each time of washing. 100 μl/well of TMB substrate (3,3',5,5'-tetramethylbenzidine) was added to the wells. The plates were incubated at room temperature at dark place for 20 minutes. 2M $H_2SO_4$ was used to terminate the reaction. Within 10 minutes after the reaction, optical density (OD) was read at 450 nm on the BOBRAD Model 550 plate reader with the blank wells of the plates was set to 0.

Data Analysis:

The average optical density (OD) values were calculated from quadruplicate values.

Corrected OD=Average OD of AGE-BSA wells− Average OD of BSA wells

The breaking rate was expressed as the percent decrease in OD:

[(Average OD of PBS wells−Average OD of test compound wells)/Average OD of PBS wells]×100%

The breaking rates of the test compounds at concentrations of 0.1, 0.3 or 1 mmol/L or a more low concentration as determined according to the above protocol are shown in Table 1 (the results are averages of more than three screening results).

TABLE 1

Breaking rates of the compound on AGE-BSA-collagen cross-links determined by ELISA

| Compound | Breaking rate (decrease % in OD) | |
|---|---|---|
| | 0.01 (umol/L) | 0.1 (umol/L) |
| A | 8.1 ± 4.76, n = 5 | 11.3 ± 7.70, n = 5 |

Example 6

Assay for In Vitro Breaking IgG Cross-Linked on Red Blood Cell Surface

Method for treatment of blood cells: blood was taken from carotid artery of postanesthetic diabetic rats of 16-week age, added with heparin for anticoagulation, centrifuged at 4° C. and 1000 g for 3 min, a lower layer of red blood cells (RBC) was obtained; washed with 0.1 mol/L PBS (pH7.4) for 3 times, centrifuged at 4° C. and 1000 g for 3 min per time; the lower layer of RBC was used in the experiment.

In vitro administration: 0.1 mol/L isoosmia PBS (pH7.4) was used as negative control, and it was used as solvent to form drug solutions of the compounds to be tested with different concentrations. Per 900 μl drug solution or solvent control was added with 100 μl RBC, slightly shaken at 37° C. for 16-18 h; centrifuged at 1000 g and 4° C. for 3 min, supernatant was discarded, 0.1 mol/L is PBS (pH7.4) was used to wash plate for 4 times to remove residual compound;

centrifuged at 1000 g and 4° C. for 3 min, a lower layer of RBC was obtained, diluted by 1:100 and used for ELISA assay.

Immunoadsorption assay protocol for IgG content cross-linked on RBC surface: Multiscreen-HA 0.45 μm 96 well microtiter plate (Millipore) was blocked with Superblock (300 μl/well) at 37° C. for 1 h; then dried at a reduced pressure of 5 mmHg, the plate was washed with PBST for 3 time, with 0.1 MPBS (pH7.4) for 3 times, and the plate was shaken for 1 min per time; the RBC to be tested was added (50 μl/well), and PBS background control wells were set (OD0); dried by suction at a reduced pressure; washed with 0.1mol/L PBS (pH7.4) 150 μl for 4 time, the plate was shaken for 1 min per time. After dried by suction at a reduced pressure, 1:500 diluted goat anti-mouse IgG-HRP (50 μl/well) was added, stood at room temperature for 2 h, dried by suction; washed with 0.1 mol/L PBS (pH7.4) 150μl/well for 3 times, the plate was shaken for 1 min per time; dried by suction; o-phenylene diamine (OPD) substrate coloration solution (100 μl/well) was added, stood at room temperature for 30 min under protection from light, the reaction was terminated with 2 mol/L $H_2SO_4$ (100 μl/well); the reaction liquid was quickly drawn off (150 μl/well) and transferred to a normal 96 well enzyme labeled plate, and OD values were measured at 490 nm.

Calculation of breaking rate of the tested compounds:

Corrected OD=average OD of RBC sample to be tested– average OD of PBS background wells without RBC, the breaking rate of the compounds is expressed as the percentages of $OD_{490\,nm}$ decrease: ($OD_{490\,nm}$ of PBS wells–$OD_{490\,nm}$ of the compound to be tested)/$OD_{490\,nm}$ of PBS wells×100%.

| | Breaking rate (OD decrease, %) | | | |
|---|---|---|---|---|
| Compound | 1 μM | 10 μM | 30 μM | 100 μM |
| A | 25.6 ± 2.1 | 26.9 ± 3.0 | 21.6 ± 5.0 | 26.0 ± 2.7 |

Example 7

Assay for Improving Vascular Compliance in Rats

Rats were anesthetized with pentobarbital sodium injection (0.8%, 50 mg/kg), subjected to tracheal cannula, heparin anticoagulation, right common carotid artery cannula, communicated with Biopac physiological recorder via is pressure transducers to record blood pressure; subjected to thoracotomy at middle of sternum, separation of ascending aorta which was covered with pulse Doppler probe, and the pulse Doppler rheometer was linked to the Biopac physiological recorder for real-time recording and calculating hemodynamic parameters by the software of Biopac (Acknowledge, Version 3): systolic blood pressure (SBP), diastolic blood pressure (DBP), heart rate (HR), cardiac output (CO), cardiac index (CI), total peripheral resistance (TPR), total peripheral resistance index (TPR Index), stroke volume (SV) and system arterial compliance (SAC), etc. After 10 min of postoperative stabilization, these parameters were recorded continuously, and mean values for 30 s were used as the measured values of these parameters.

Formula for calculating some of hemodynamic parameters:

$$TPR = \text{mean arterial pressure (MAP)}/CO$$

$$SAC = SV/(SBP-DBP)$$

As compared to the normal control, the diabetic model rats show a significant decrease in body weight and heart rate (P<0.01), while systolic pressure and diastolic pressure show no significant change (Table 1-1), each of organs shows an significant increase of organ index (P<0.01) (Table 1-2). As compared to model rats, the rats of medication administration group show no significant change in body weight, heart rate, systolic pressure, diastolic pressure and indexes of organs.

TABLE 1-1

Blood pressure and heart rate measured in diabetic rats treated with compound A for 4 weeks

| Group | Dose (mg/kg) | Body weight (g) | Systolic pressure (mmHg) | Diastolic pressure (mmHg) | Heart rate (beats/min) |
|---|---|---|---|---|---|
| Normal | | 447 ± 29 | 105.7 ± 10.1 | 72.5 ± 11.4 | 340.0 ± 20.2 |
| Diabetic | | 346 ± 20## | 108.8 ± 11.3 | 70.4 ± 14.4 | 297.6 ± 37.6## |
| A | 9(i.g.) | 341 ± 27 | 105.3 ± 12.0 | 68.8 ± 14.0 | 265.2 ± 25.8 |
| | 18(i.g.) | 344 ± 24 | 108.7 ± 14.7 | 72.8 ± 17.2 | 282.2 ± 31.9 |
| | 36(i.g.) | 342 ± 28 | 99.2 ± 13.2 | 60.7 ± 16.1 | 261.0 ± 32.3 |

P < 0.01 vs. normal group

TABLE 1-2

Parameters of organs (n = 9-12, Mean ± SD)

| Group | Heart | Heart ventricle | Left ventricle | Left kidney | Right kidney |
|---|---|---|---|---|---|
| Normal | 2.49 ± 0.08 | 2.23 ± 0.07 | 1.76 ± 0.08 | 2.69 ± 0.16 | 2.77 ± 0.17 |
| Diabetic | 3.47 ± 0.34## | 3.04 ± 0.29## | 2.45 ± 0.28## | 5.14 ± 0.34## | 5.28 ± 0.36## |
|  | 3.42 ± 0.21 | 2.99 ± 0.14 | 2.29 ± 0.10 | 5.20 ± 0.42 | 5.33 ± 0.39 |
| A | 3.44 ± 0.19 | 3.01 ± 0.17 | 2.34 ± 0.12 | 5.16 ± 0.42 | 5.22 ± 0.39 |
|  | 3.44 ± 0.18 | 3.03 ± 0.16 | 2.32 ± 0.15 | 5.07 ± 0.37 | 5.19 ± 0.33 |

Organ parameters (g/g × $10^{-3}$)

P <0.01 vs. normal group

Doppler rheometer was used to measure SBP, DBP, HR in the rats, and the CO, CI and SAC of the rats were calculated. It can be seen from Table 1-3, in comparison with normal rats, diabetic rats show a significant decrease in CO, CI and SAC (P<0.01), and a significant increase in TPR and TPRI (P<0.01); this indicate that the diabetic rats have a significant increase of total peripheral resistance and a significant decrease of cardiac output and system compliance, exhibiting the sclerosis of the cardiovascular system and other structural and functional disorders in long-term diabetic rats. In comparison with the model group of diabetic rats, after 4 weeks of medication administration, all rats of medication administration group show a significant increase in CO, CI and SAC, and a significant decrease in TPR and TPRI. This indicates that compound A has an effect of improving angiosclerosis in long-term diabetic rats.

TABLE 1-3

Hemodynamics measured in diabetic rats and diabetic rats treated with compound A for 4 weeks (n = 9-12)

| Group | Dose (mg/kg) | CO (ml/min) | CI (ml/min per $cm^2$) | TPR ($10^3 \cdot$ dyne $\cdot sec/cm^5$) | TPR index (dyne $\cdot sec/cm^3$) | SAC ($10^{-3}$ ml/mmHg) |
|---|---|---|---|---|---|---|
| Normal |  | 124.6 ± 20.3 | 0.214 ± 0.040 | 83.8 ± 21.1 | 142.8 ± 33.8 | 13.8 ± 3.6 |
| Diabetic |  | 60.3 ± 7.9## | 0.134 ± 0.016## | 109.87 ± 19.0## | 241.3 ± 19.0## | 5.55 ± 0.94## |
| A | 9 (i.g.) | 84.9 ± 13.6** | 0.194 ± 0.031** | 78.6 ± 19.7** | 181.6 ± 51.3** | 9.05 ± 1.44** |
|  | 18 (i.g.) | 79.2 ± 10.6** | 0.179 ± 0.026** | 87.4 ± 22.3* | 198.2 ± 56.2* | 8.02 ± 1.27** |
|  | 36 (i.g.) | 77.7 ± 10.0** | 0.179 ± 0.024** | 77.0 ± 19.6** | 176.4 ± 44.6** | 7.92 ± 1.11* |

Cardiac index: CO corrected for body surface area;

TPR index: TPR corrected for body surface area.

P < 0.05,

P < 0.01 vs. Normal;

*P < 0.05,

**P < 0.01 vs. Diabetic

TABLE 1-4

Influence of compound A on LV function of diabetic rats (n = 8-10)

| Group | Dose (mg/kg) | HR (beat/min) | LVSP (mmHg) | Pos dp/dt (mmHg/s) | Neg dp/dt (mmHg/s) | LVEDP (mmHg) |
|---|---|---|---|---|---|---|
| Normal |  | 430.46 ± 23.82 | 191.68 ± 22.03 | 15861.8 ± 3093.2 | 12724.3 ± 2299.0 | 1.50 ± 0.87 |
| Diabetic |  | 359.56 ± 32.91# | 153.49 ± 20.05# | 9410.2 ± 1294.2# | 6684.2 ± 1400.7# | 8.16 ± 3.05# |
| A | 9 (i.g.) | 361.80 ± 39.74 | 161.54 ± 13.98 | 12201.2 ± 1872.2** | 7762.8 ± 320.2* | 5.73 ± 1.44** |
|  | 18 (i.g.) | 377.35 ± 17.54 | 170.65 ± 8.94** | 11712.8 ± 1370.9** | 7660.8 ± 1154.8 | 6.87 ± 1.26* |
|  | 36 (i.g.) | 368.99 ± 31.66 | 168.25 ± 15.48* | 11425.3 ± 1660.0* | 7675.4 ± 2216.6 | 6.79 ± 2.47* |

LVSP: left ventricular systolic pressure;

LVEDP: left ventricular end diastolic pressure.

P < 0.05,

P < 0.01 vs. Normal;

*P < 0.05,

**P < 0.01 vs. Diabetic

Example 8

Assay for Improving Left Ventricular Function in Rats

Rats were anesthetized with pentobarbital sodium injection (0.8%, 50 mg/kg), subjected to tracheal cannula, heparin anticoagulation, right common carotid artery cannula to left ventricle, communicated with Biopac physiological recorder via pressure transducers to record left ventricular pressure tracing, and the software of Biopac (Acknowledge, Version 3) was used for real-time reacording: heart rate, left ventricular systolic pressure peak (LVSP), maximum rate of change of left intraventricular pressure (±dp/dtmax), left ventricular end diastolic pressure (LVEDP). After 10 min of postoperative stabilization, the above parameters were recorded continuously, and mean values for 30 s were used as the measured values of these parameters. The results are shown in Table 1-4.

As compared to the normal control group, the rats of diabetic group show a significant decrease in heart rate, LVSP, +dp/dt and −dp/dt (P<0.01), and meantime a significant increase in LVEDP (P<0.01), which indicate the left is ventricular dysfunction of diabetic rats. As compared to the diabetic model group, after 4 weeks of medication administration, all rats of medication administration group show a signfiicant increase of +dp/dt; a significant decrease of LVEDP (P<0.05 or P<0.01); a significant increase of LVSP, except for the group of A 9 mg/kg (P<0.05 or P<0.01); a significant increase of −dp/dt for the group of A 9 mg/kg (P<0.05), the groups of A 18 mg/kg and A 36 mg/kg give P values of 0.055 and 0.057, respectively, also exhibiting an increasing tendency. These indicate that A is able to improve heart systolic dysfunction caused by diabetes, and has a significant effect in improving left ventricular functions (Table 1-4).

Example 9

Experiment on Dissolubility of Rat Tail Collagen

Tail tendon collagen fibrils were taken out under ice-bath, washed with physiological saline, peeled off non-collagen tissues, lyophilized and stored at −70° C. for standby use.

The lyophilized tail collagen was cut into pieces, 2 mg of tail collagen was precisely weighed, added with 10 µg/ml pepsin (solvent: 0.5 mol/L acetic acid) to reach a final concentration of 5 µg pepsin/mg tail collagen, shanken at 4° C. for 2 h, centrifuged at 40000 g for 60 min, after the volume of supernatant was precisely measured, 500 µl of supernatant and total deposition were separately transferred into 5 ml ampules, added with 6 mol/L HCl, sealed, placed in calorstat oven, and hydrolyzed at 110° C. for 24 h.

Measurement of hydroxyproline concentration in the hydrolysis solution: (1) 100 µl of hydrolysis solution was taken from each of ampules, added with about 50 µl 10 mol/L NaOH to pH 6.0, and citric acid buffer solution (50 g citric acid.H$_2$O, 72.36 g anhydrous sodium acetate, 34 g NaOH, 11.52 ml glacial acetic acid were mixed and added with water to 1200 ml, and added with 300 ml n-propanol) 850 µl. (2) Chloramine T (1.41 g chloramines T was dissolved in 10 ml of distilled water, then separately added with 10 ml n-propanol and 80 ml citric acid buffer solution) 500 µl was added, mixed homogeneously, and the reaction was conducted at room temperature for 10 min. (3) 3.15 mol/L perchloric acid 500 µl was added, mixed quickly at room temperature for 5 min. (4) 10% P-DMAB (1 g p-dimethylaminobenzaldehyde, added with 3.15 mol/L perchloric acid 2.6 ml to dissolve, then diluted with n-propanol to 10 ml, ready to use) 500 µl was added, mixed quickly at 75° C. water-bath for 10 min. (5) the reaction solution was cooled quickly in ice-water, and absorbance value was measured by ELIASA at 570 nm. (6) the hydroxyproline concentration in the hydrolysis solution was calculated by using a correspondingly synchronically measured hydroxyproline standard curve (0, 0.5, 1, 2, 3, 4, 5 and 6 µg/ml). The dissolubility of tail collagen is obtained by using the following formula:

$$\text{Dissolubility of tail collagen \%} = \frac{\text{Total hydroxyproline content of supernatant}}{\text{Hydroxyproline content of supernatant} + \text{Total hydroxyproline content of deposition}} \times 100\%$$

In comparison with the normal control group, the rats of diabetic model group show a significant decrease of tail collagen dissolubility (19.7±7.2 vs. 79.8±12.0%, P<0.01). As compared to the diabetic model group, the groups of A 18 mg/kg and A 36 mg/kg show a significant increase of tail collagen dissolubility in diabetic rats (33.7±17.8, 37.5±11.1 vs. 19.7±7.2%, P<0.01).

Example 10

Experiment on Increasing Cardiac Muscle Collagen Dissolubility in Rats

After the end of vascular compliance experiment, the heart of each of rats was taken, trimmed to remove heart auricle and right ventricle and remain only left ventricle, the trimmed tissue block was planced in a mortar, added with a small amount of liquid nitrogen and ground rapidly, added with a small amount of liquid nitrogen again when the tissue became soft and ground continuously to form a fine powder, and stored at −70° C. for standby use. About 100 mg of cardiac muscle was weighed, added with 1 ml 200 µg/ml pepsin (solvent: 0.5 mol/L acetic acid), shaken at 37 ° C. for 2 h and 24 h, respectively, centrifuged at 40000 g for 60 min, the supernatants of pepsin digestion solutions for 2 h and 24 h were separately taken, hydrolyzed and measured to determine hydroxyproline contents (the methods for hydrolysis and measurement are the same as aforementioned). The dissolubility of cardiac muscle collagen is calculated by the following formula:

$$\text{Dissolubility of cardiac muscle collagen \%} = \frac{\text{Hydroxyproline content of supernatant of 2 h peppsin digestion solution}}{\text{Hydroxyproline content of supernatant of 24 h peppsin digestion solution}} \times 100\%$$

In comparison with the normal group, the rats of the diabetic model group show a significant decrease of left ventricular cardiac muscle collagen dissolubility (42.8±4.3% vs. 68.9±14.1%, P<0.01). As compared to the diabetic model group, the group of A 18 mg/kg shows a significant increase of cardiac muscle collagen dissolubility in diabetic rats (54.7±11.0, 53.7±11.9, 57.7±7.3 vs. 42.8±4.3%, P<0.01).

The results of Examples 5-10 indicate that compound A has effects of breaking the cross-linking structure of AGEs in vitro; significantly decreasing AGEs fluorescence content in aorta, left ventricular cardiac muscle and kidney in long-term diabetic rats, and in the meantime, improving the dissolubility of cardiac muscle collagen and tail collagen, as well as improving aortic compliance in rats, reducing total peripheral resistance, increasing cardiac output, and significantly improving left ventricular function. Hence, the compound A can break already formed AGEs cross-links, reconstruct the vascular structure, reverse sclerosis and dysfunction of the cardiovascular system induced by diabetes, and is a novel AGEs breaker.

Example 11

Experiment on Enhancing the Sensitivity to Cardiovascular Medications in Senior and Diabetic Patients The experiment about influence of AGEs breaker on hypotensive effect of nifedipine was performed on a diabetic-hypertension rat model. Test animals and diabetic-hypertension models were rats selected for confirming the establishment of model by comparing to a control group. During the experiment, the animals took food freely, and were not interfered with any hypoglycemic drugs or hypotensive drugs.

Animal grouping and administration modes:

The compound A was dissolved in distilled water, ready for use. Rats were randomly grouped as diabetic-hypertension control (DM-HTN) group and A (18 mg/kg) group. The drug was introgastrically administered once per day, and an equal amount of distilled water was administered in the diabetic-hypertension control group, for consecutive 4 weeks. After the end of experiment, blood samples were taken, thoracic aorta, liver, kidney were stored at −70° C. for standby use, and used for assays for tissue biochemical indicators and gene expression. Another part of kidney was fixed with 4% paraformaldehyde and used for pathological staining.

Preparation of nifedipine solution:

Nifedipine powder was formulated with DMSO to form a 5 mg/ml solution, then diluted with 15% ethanol-10% DMSO-25% PEG400 to form a 500 µg/ml solution, and diluted again to form 125 µg/ml, 62.5 µg/ml, 31.25 µg/ml, 15.62 µg/ml, 7.8 µg/ml solutions.

Method for studying the influence of AGEs breaker on the hypotensive effect of nifedipine Rats were anesthetized with urethane-chloralose mixture by i.p., subjected to heparin anticoagulation, right common carotid artery cannula, communicated with Biopac physiological recorder via pressure transducers. Through a right femoral vein remaining needle, nifedipine solutions were injected slowly by 5 batches in an order of concentrations from low to high, and arterial systolic pressure, diastolic pressure, pulse pressure and heart rate change were recorded continuously.

Influence of AGEs breaker on blood pressure in diabetic-hypertension rats

The results of blood pressure in vivo measured in rats show that the diabetic-hypertension rats administered with the compound A for 4 weeks give no significant change in heart rate and blood pressure. This indicates that the AGEs breaker has no direct influence on blood pressure of diabetic-hypertension rats. (Table 2-2)

TABLE 2-2

Blood pressure and heart rate measured in rats
(n = 12 Mean ± SD)

| Group | HR (beat/min) | SBP (mmHg) | DBP (mmHg) | MBP (mmHg) | PP (mmHg) |
|---|---|---|---|---|---|
| DM-HTN | 423.8 ± 38.5 | 165.8 ± 14.1 | 145.9 ± 13.4 | 152.3 ± 16.9 | 19.8 ± 4.6 |
| A | 408.7 ± 35.7 | 166.6 ± 12.4 | 144.2 ± 11.1 | 153.5 ± 13.7 | 22.9 ± 3.8 |

Influence of the AGEs Breaker on Hypotensive Effect of Nifedipine

The hypotensive effect of a hypotensive drug in diabetic-hypertension rats was observed by administering the drug in a gradient concentration from low to high. From the administration of the second dosage of nifedipine (15.62 µg/ml), the compound A group stated to show an increased hypotensive effect in comparison with the diabetic-hypertension model group; when using the third dosage (31.25 µg/ml), the hypotensive extent of nifedipine in the rats of the compound A group was significantly higher than that of the model group (19.49±13.29 vs. 9.35±6.46 mmHg, P<0.05); when using the forth dosage (62.5 µg/ml), the compound A group shows an enhanced effect (29.99±9.06 vs. 18.92±10.54 mmHg), in comparison with the model group, P<0.05. This indicates that the treatment with AGEs breaking compound A can enhance the susceptibility of diabetic-hypertension rats to nifedipine.

In the present experiment, after 4 weeks of pre-treatment with the compound A in diabetic-hypertension rats, a classical method of evaluating hypotensive drugs was used, hypotensive nifedipine acting on vascular sooth muscle cells was administered in a gradient from low to high concentration, with the increase of concentration, the hypotensive effect of nifedipine on the rats of the compound A group became better than that of the hypertension model group, when the concentration of nifedipine increased to 31.25 µg/ml, the hypotensive extent in the group of the AGEs breaking compound A had a significant statistic difference from that of the hypertension model group. This indicates that the AGEs breaking compound A surely has effects of enhancing the hypotensive effect of nifedipine, and can enhance the sensitivity to cardiovascular medication in senior and diabetic patients.

Example 12

Pharmacodynamic Experiment for Treating Chronic Heart Failure

Animal grouping and administration manner:

First batch: NaCl treated diabetic rats modeled with heart failure for 20 weeks were divided into 4 groups: model control group (Model Control), valsartan group (VAL, ig, 10 mg/kg), the compound A group (ig, 18 mg/kg), administered with drug once per day for consecutive 16 weeks. The pharmacodynamic evaluation was conducted by using a noninvasive ultrasonic cardiogram method.

Second batch: NaCl treated diabetic rats modeled with heart failure for 20 weeks and normal control rats synchronically and conventionally drinking water were divided into 5 groups: normal control rats synchronically and conventionally drinking water group (Normal Control), model control group (Model Control), the compound A group (ig, 9 mg/kg), the compound A group (ig, 36 mg/kg), administered with drug once per day for consecutive 10 weeks. The pharmacodynamic evaluation on left ventricular function was conducted by using a ventricular chatheterization method.

Evaluation indexes: (1) morphology indexes: left ventricular posterior wall dimensions (LVPWd), left ventricular diastasis internal diameter (LVDd), end systolic diameter (LVDs); (2) functional indexes: ejection fraction (EF), shortening fraction (FS), ventricular early blood flow filling rate (E), atrial filling rate (A) and ratio of E/A; Doppler tissue image; at cardiac apical four chamber view, the valve ring of anterior mitral valve was used as sampling point, peak early diastolic velocity (Ea peak), peak late diastolic velocity (Aa peak), and Ea/Aa ratio reflected the systolic and diastolic motion of the whole left ventricle.

SPSS statistic software was used to analyze and treat data, and all data were expressed in mean±standard deviation (Mean±SD). In the results of the experiment, the significance test of inter-group difference was statistically treated by using one-way ANOVA analysis method, and significant difference was determined when $P<0.05$.

Pharmacodynamic Evaluation Results of the First Batch Model

Results of ultrasonic cardiogram evaluation:

Morphology indexes: in the $30^{th}$ week of modeling (the $10^{th}$ week of is administration), the ultrasonic cardiogram shows, in comparison with the diabetic model rats treated with NaCl by drinking water, after intragastric administration for 10 weeks, the rats of valsartan group (10 mg/kg) and the compound A group (18 mg/kg) exhibited a slight increase in PWd and a slight decrease in LVDd and LVDs.

after 16 weeks of intragastric administration, the rats of valsartan group (10 mg/kg) and the compound A group (18 mg/kg) exhibited a significant decrease in E/A ratio (model control 2.5±0.52; valsartan group 1.32±0.25; the compound A group 1.45±0.18, $P<0.05$ or $P<0.01$); and valsartan (10 mg/kg) can significantly increase the Ea/Aa ratio in rats ($P<0.01$); which indicates that in the $36^{th}$ week, the administration of valsartan and the compound A for 16 weeks can is significantly improve the left ventricular diastolic function in diabetic rats treated with NaCl by drinking water.

Evaluation Results of the Second Batch of Model

Influence on left ventricular function and blood plasma BNP level in rats of the compound A group As shown in Table 3-1, in comparison with the normal control group, the diabetic rats treated with NaCl in drinking water exhibited a significant decrease in +dp/dt and −dp/dt, and in the meantime, a significant increase in LVEDP and blood plasma BNP level, which indicates a significant decrease in both systolic and diastolic functions of ventricle. The rats of the compound A groups (9 and 36 mg/kg) all exhibited a significant increase in +dp/dt and −dp/dt ($P<0.05$ or $P<0.01$) and a significant decrease in LVEDP ($P<0.01$). This indicates that the compound A can improve the diastolic function of ventricle in diabetic rats treated with NaCl in drinking water.

TABLE 3-1

Effects of A on LV function in diabetic rats treated with NaCl (n = 8-10)

| Group | Dose Mg/kg | Body weight g | Heart rate Beats/min | LVSP mmHg | Pos dp/pt mmHg/s | Neg dp/pt mmHg/s | LVEDP mmHg | BNP Pg/ml |
|---|---|---|---|---|---|---|---|---|
| NC |   | 549 ± 52 | 419.5 ± 30.4 | 196.6 ± 20.3 | 17770 ± 4736 | 14009 ± 4809 | 8.9 ± 3.8 | 43.8 ± 7.9 |
| MC |   | 283 ± 28[b] | 405.6 ± 34.7 | 178.9 ± 27.8 | 11548 ± 2836[b] | 6597 ± 1128[b] | 21.3 ± 5.3[b] | 53.1 ± 11.3[b] |
| A | 9 | 282 ± 47 | 418.3 ± 27.2 | 187.6 ± 22.3 | 10729 ± 2035[d] | 10729 ± 2035[d] | 11.6 ± 2.9[d] | 50.8 ± 5.7 |
|   | 36 | 299 ± 42 | 406.1 ± 32.9 | 189.2 ± 13.8 | 10033 ± 2044[d] | 10033 ± 2044[d] | 13.0 ± 6.1[d] | 51.3 ± 8.1 |

LVSP: left ventricular systolic pressure; LVEDP: left ventricular end diastolic pressure; BNP: B-type natriuretic peptide; NC: normal control; MC: model control
[a]$P<0.05$,
[b]$P<0.01$ vs. NC;
[c]$P<0.05$,
[d]$P<0.01$ vs. MC The ultrasonic cardiogram in the $36^{th}$ week of modeling (the $16^{th}$ week of administration) shows that, in comparison with the diabetic model rats treated with NaCl by drinking water, after 16 weeks of intragastric administration, the rats of all administration groups exhibited similar results in the change tendency of left ventricular morphology indexes as those measured in the $30^{th}$ week of modeling (the $10^{th}$ week of administration).

Left ventricular diastolic function indexes:

In the $30^{th}$ week of modeling (the $10^{th}$ week of administration), the ultrasonic cardiogram shows, in comparison with the diabetic model rats treated with NaCl by drinking water, after 10 weeks of intragastric administration, the rats of valsartan group (10 mg/kg) and the compound A group (18 mg/kg) exhibited a significant decrease in E/A ratio (model control 2.5±0.31; valsartan group 1.24±0.32; the compound A group 1.32±0.31, $P<0.05$ or $P<0.01$), in the meantime, the Ea/Aa ratio increased significantly ($P<0.05$ or $P<0.01$,); which indicates that in the $30^{th}$ week of modeling, the administration of valsartan and the compound A for 10 weeks can s significantly improve the left ventricular diastolic function in diabetic rats treated with NaCl by drinking water.

In the $36^{th}$ week of modeling (the $16^{th}$ week of administration), the ultrasonic cardiogram shows, in comparison with the diabetic model rats treated with NaCl by drinking water,

What is claimed is:

1. A crystal of a compound of Formula I,

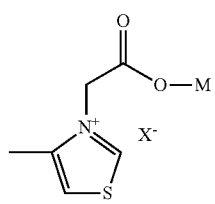

I wherein:

M is Na and X is Br, which crystal has the following crystallographic data: $C_{12}H_{14}Br_2N_2Na_2O_4S_2$, Mr=520.20, triclinic system, space group P-1, crystallographic parameters: a =8.9000(18)Å, α=92.82(3) deg., b =9.4095(19) Å, β=109.00(3) deg., c =12.028(2) Å, and δ=104.11(3) deg.

2. A pharmaceutical composition comprising the crystal of claim 1 and a pharmaceutically acceptable carrier or excipient.

3. A method for treating or relieving a disease associated with protein aging, the method comprising the step of administering to a subject in need thereof an effective amount of the crystal of claim 1.

4. A method for reversing tooth staining in an animal, the method comprising the step of administering to a subject in need thereof an effective amount of the crystal of claim 1.

5. A method for (i) improving skin elasticity or reducing skin wrinkles, (ii) treating diabetes, (iii) treating or relieving a sequela of diabetes, (iv) treating or relieving a kidney injury, (v) treating or relieving a vascular injury, (vi) treating or relieving hypertension, (vii) treating or relieving retinopathy, (viii) treating or relieving a lens protein injury, (ix) treating or relieving cataract, (x) treating or relieving peripheral nerve diseases, or (xi) treating or relieving osteoarthritis, which method comprises administering to a subject in need thereof the crystal of claim 1.

\* \* \* \* \*